US00PP13807P39

(12) United States Plant Patent
Pieters

(10) Patent No.: US PP13,807 P3
(45) Date of Patent: May 13, 2003

(54) CHRYSANTHEMUM PLANT NAMED 'GEDI ONE GAL'

(75) Inventor: Dirk Pieters, Staden (BE)

(73) Assignee: Pieters Plant Production, Bvba, Oostnieuwkerke (BE)

( * ) Notice: Subject to any disclaimer, the term of this patent is extended or adjusted under 35 U.S.C. 154(b) by 0 days.

(21) Appl. No.: 09/873,921

(22) Filed: Jun. 4, 2001

(65) Prior Publication Data

US 2002/0188982 P1 Dec. 12, 2002

(51) Int. Cl.[7] ..... A01H 5/00
(52) U.S. Cl. ..... Plt./293
(58) Field of Search ..... Plt./293, 287

(56) References Cited

U.S. PATENT DOCUMENTS

PP10,207 P * 1/1998 Pieters ..... Plt./286
PP10,213 P * 1/1998 Wain ..... Plt./287

* cited by examiner

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant variety characterized by a large decorative type inflorescence, consistent flowering response to short days, blooming consistently after 49 days of short day length, free branching habit, and dark reddish-purple ray florets, which resist fading with age.

1 Drawing Sheet

LATIN NAME

*Dendranthema morifolium*

VARIETY

'GEDI ONE GAL'

BACKGROUND OF THE INVENTION

Figure 1:
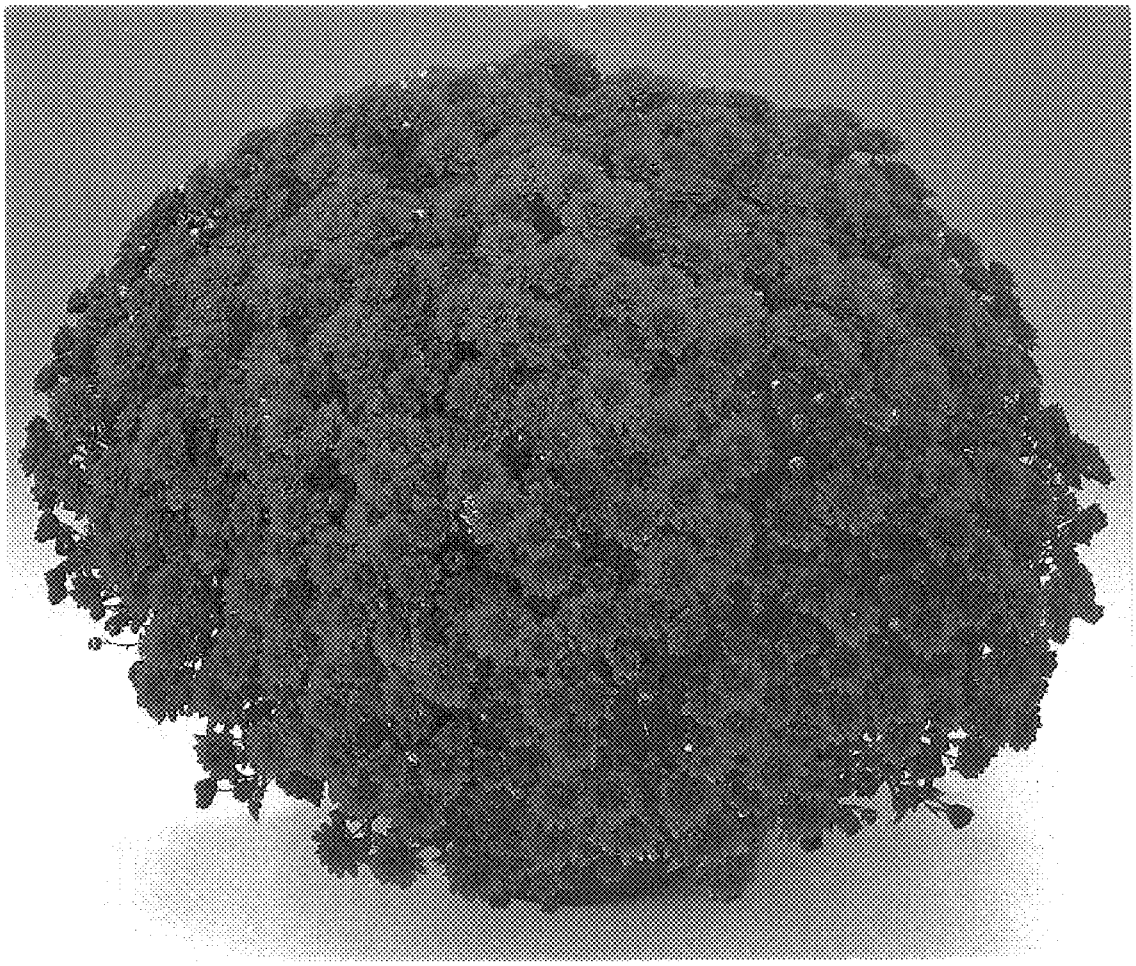

The present invention relates to a new and distinct cultivar of Chrysanthemum plant, botanically known as *Dendranthema morifolium* and herein after referred to by the cultivar name 'GEDI ONE GAL.'

This new cultivar was the result of hybridization of a female parent, 'Tripoli' (U.S. Plant Pat No. 10,207) with a male parent, 'Ampiro' (unpatented in the United States). The new cultivar was selected in October 1997.

Asexual reproduction of the new cultivar by apical tip cutting and meristem tissue culture was performed in Oxnard, Calif. and has shown that the unique features of this new cultivar are stable and reproduced true to type on successive generations.

SUMMARY OF THE INVENTION

The cultivar 'GEDI ONE GAL' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GEDI ONE GAL.' These observations were made on plants approximately 140 days old from rooted cuttings. These characteristics in combination distinguish 'GEDI ONE GAL' as a new and distinct Chrysanthemum:

1. Large decorative type inflorescence;
2. Consistent flowering response to short days, blooming consistently after 49 days of short day length;
3. Free branching habit; and
4. Dark redish-purple ray florets, resisting fading with age.

Plants of the new Chrysanthemum are similar to plants of the parent cultivars in most horticultural characteristics, however plants of the new cultivar differ from plants of the female parent cultivar 'Tripoli' in the following characteristics:

1. The new cultivar has a different bloom type;
2. The new cultivar has many more ray florets than the parent; and
3. The new cultivar has individual blooms resisting fading better.

The new cultivar also differed from the male parent 'Ampiro' in the following characteristics:

1. The new cultivar has a wider diameter flower; and
2. The new cultivar has different color ray florets.

The new cultivar can be compared to the Chrysanthemum cultivar 'Jenny Wren' (disclosed in U.S. Plant Pat. No. 10,213). However plants of the new Chrysanthemum differed from the plants of the cultivar 'Jenny Wren' in the following characteristics:

1. The new cultivar naturally blooms 2 weeks later;
2. The new cultivar has darker reddish-purple ray florets;
3. The new cultivar has a more round plant shape;
4. The new cultivar has many more ray florets; and
5. The new cultivar has ray florets which are resistant to fading.

BRIEF DESCRIPTION OF THE PHOTOGRAPHS

The photograph shows a plant of 'GEDI ONE GAL' grown in a 2-gallon container. A single cutting was used in the pot, planted mid-May and grown under outdoor field conditions.

DETAILED BOTANICAL DESCRIPTION

In the following description, color references are made to The Royal Horticultural Society Colour Chart except where general terms of ordinary dictionary significance are used. The following observations and measurements describe plants grown in a commercial field in Oxnard, Calif. in the month of September 2000. The growing conditions range from 60° to 65° F. at night to 70° to 85° F. during the day. Measurements and numerical values represent averages of typical flowering types.

Botanical classification: *Dendranthema morifolium* cultivar 'GEDI ONE GAL'.
Commercial classification: Garden-type Chrysanthemum.
Parentage: Hybridization of female parent 'Tripoli' (U.S. Plant Pat. No. 10,207) and male parent 'Ampiro' (unpatented in the United States).

PROPAGATION

Time to rooting: 7 to 14 days at approximately 21° C.
Root description: Fine, fibrous.

PLANT

Growth habit: Mounding herbaceous perennial.
Height: Approximately 28 cm.
Plant spread: Approximately 31 cm.
Growth rate: Moderate.
Branching characteristics: Free Branching.
Internode length: Approximately 2.5 cm.
Length of lateral branches: Approximately 23 cm.
Number of leaves per lateral branch: Approximately 28.
Stem color: Near 137A.

FOLIAGE

Leaf:
*Arrangement.*—Alternate, single.
*Average length.*—Approximately 7.8 cm.
*Average width.*—Approximately 5.2 cm.
*Shape of blade.*—Ovate.
*Apex.*—Acuminate.
*Base.*—Attenuate.
*Attachment.*—Stalked.
*Margin.*—Pinnately lobed and toothed.
*Texture of top surface.*—Lightly pubescent.
*Texture of bottom surface.*—Lightly pubescent.
*Color.*—Young foliage upper side: Near 137A young foliage under side: Near 137B mature foliage upper side: Near 137A mature foliage under side: Near 137B venation upper side: Near 138C venation under side: Near 137C.

Petiole:
*Average length.*—Approximately 3.0 cm.
*Color.*—Near 137A.
*Diameter.*—Approximately 0.3 cm.

BLOOM

Inflorescence:
*Flowering habit.*—Induced by darkness period greater than 13.5 hours, approximately 49 days of appropriate day length required to induce and develop blooms.
*Inflorescence form.*—Decorative.
*Natural flowering season.*—Approximately the last week in September, first week in October.
*Number of inflorescences per stem.*—Approximately 15.
*Inflorescence diameter.*—Approximately 8.0 cm.
*Inflorescence depth.*—2.2 cm.
*Inflorescence longevity on plant.*—Approximately 24–29 days.
*Persistence.*—Persistent.

Ray florets:
*Appearance.*—Matte.
*Texture.*—Smooth.
*Average number per flower.*—*270.*
*Shape.*—Oblanceolate.
*Margin.*—Entire.
*Apex.*—Obtuse.
*Length.*—Approximately 3.9 cm.
*Width.*—Approximately 1 cm.
*Color.*—Upper surface at first opening: Near 59A upper surface at maturity: Near 59B upper surface at fading: Near 53B under surface at first opening: Near 53A under surface at maturity: Near 53B under surface at fading: Near 53B.

Disc florets:
*Appearance.*—Shiny.
*Texture.*—Smooth.
*Average number per flower.*—Approximately 40.
*Shape.*—Cylindric.
*Apex.*—Obtuse.
*Average length.*—Approximately 1 cm.
*Average width.*—Approximately 0.2 cm.
*Color.*—At first opening: Near 2A at maturity: Near 21A at fading: Near 17D.

Peduncle:
*Length.*—At terminal end (shortest): Approximately 7 cm at lateral end (longest): Approximately 11 cm.
*Diameter.*—Approximately 0.4 cm.
*Strength.*—Moderate.
*Color.*—Near 137C.
*Habit.*—Erect.
*Surface texture.*—Pubescent.

Inflorescence bud:
*Length.*—Approximately 1 cm.
*Diameter.*—Approximately 1 cm.
*Form.*—Globular.
*Color.*—Near 59A.

Phyllaries:
*Appearance.*—Matte.
*Texture.*—Lightly pubescent.
*Number.*—Approximately 60 to 70.
*Shape.*—Ovate.
*Margin.*—Entire.
*Apex.*—Acute.
*Diameter.*—Approximately 0.4 cm.
*Length.*—Approximately 0.6 cm.
*Color.*—Upper side: Near 137A under side: Near 137A.

REPRODUCTIVE ORGANS

Ray florets:
*Number of pistils per flower.*—1.

*Stigma shape.*—2 branched.
*Stigma color.*—Near 7A.
*Style color.*—Near 16D.
*Style length.*—Approximately 0.5 cm.
*Stamens.*—Absent.

Disc florets:
*Number of pistils per flower.*—1.
*Stigma shape.*—Cylindric.
*Style length.*—Approximately 0.5 cm.
*Number of stamens per flower.*—Approximately 5.
*Anther shape.*—Tubular.
*Anther color.*—Near 6A.
*Pollen color.*—Near 7B.

OTHER CHARACTERISTICS

Seed production: Commercially, this plant is not used or observed in a stage wherein seeds would be produced. Therefore, seed production has not been observed.

Flower fragrance: Absent.

Disease resistance: Neither resistance nor susceptibility to diseases and pests have been observed in this cultivar.

What is claimed is:

1. A new and distinct variety of Chrysanthemum plant named 'GEDI ONE GAL' as herein illustrated and described.

* * * * *